(12) United States Patent
Al-Farhan et al.

(10) Patent No.: US 6,281,367 B1
(45) Date of Patent: Aug. 28, 2001

(54) PROCESS FOR THE SYNTHESIS OF HIV PROTEASE INHIBITORS

(75) Inventors: Emile Al-Farhan, Devens; David D. Deininger, Cambridge, both of MA (US); Stephen McGhie, Dartford (GB); John O'Callaghan, Kemsing (GB); Mark Stuart Robertson, Frindsbury (GB); Keith Rodgers, Robertsbridge (GB); Stephen John Rout; Hardew Singh, both of Dartford (GB); Roger Dennis Tung, Cambridge, MA (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/646,277

(22) PCT Filed: Mar. 18, 1999

(86) PCT No.: PCT/GB99/00852

§ 371 Date: Dec. 12, 2000

§ 102(e) Date: Dec. 12, 2000

(87) PCT Pub. No.: WO99/48885

PCT Pub. Date: Sep. 30, 1999

(30) Foreign Application Priority Data

Mar. 20, 1998 (GB) .................................................. 9805898

(51) Int. Cl.$^7$ .................................................. C07D 307/02
(52) U.S. Cl. .............................................. 549/475; 564/87
(58) Field of Search .................................. 564/87; 549/475

(56) References Cited

FOREIGN PATENT DOCUMENTS

WO 94/05639 * 3/1994 (WO) .

OTHER PUBLICATIONS

Knipe, A et al 'Kinetics of desulphonative double smiles rearrangement of N–(2–hydroxyalkyl)–p–nitrobenzenesulphonamides' Journal of the Chemical Soc., Perkin Trans. 2, p1741–2–8, 1976.*

Maligres, P et al 'Nosylazridines; activated aziridine electrophiles 'Tetrahedron Letters, vol. 38 p. 5253–6, 1997.*

* cited by examiner

*Primary Examiner*—Amelia Owens
(74) *Attorney, Agent, or Firm*—Karen L. Prus

(57) ABSTRACT

An improved process for the synthesis of (3S)-tetrahydro-3-furyl N-[(1S,2R)-3-(4-amino-N-isobutylbenzenesulphonamido)-1-benzyl-2-hydroxypropyl] carbamate comprising four steps form the compound of formula A and a novel intermediate thereto.

12 Claims, No Drawings

PROCESS FOR THE SYNTHESIS OF HIV PROTEASE INHIBITORS

This application is filed pursuant to 35 U.S.C. §371 as a U.S. National Phase Applicatiion of International Application No. PCT/GB99/00852 filed Mar. 18, 1999, which claims priority from GB9805898.5 filed Mar. 20, 1998.

This invention relates to a new process for the synthesis of (3S)-tetrahydro-3-furyl N-[(1S,2R)-3(4-amino-N-isobutylbenzenesulphonamido)-1-benzyl-2-hydroxypropyl] carbamate, hereinafter referred to as the compound of formula (I), and to novel intermediates thereto.

The compound of formula (I) has the following structure

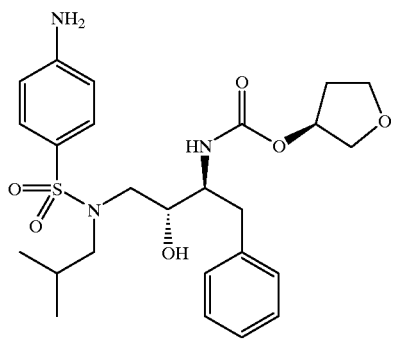

(I)

and was first described in PCT patent publication number WO94/05639 at Example 168. Currently there is considerable interest in the compound of formula (I) as a new chemotherapeutic compound in the treatment of human immunodeficiency virus (HIV) infection and the associated conditions such as acquired immune deficiency syndrome (AIDS) and AIDS dementia.

There exists at the present time a need to produce large quantities of the compound of formula (I) for clinical investigation into the efficacy and safety of the compound as a chemotherapeutic agent in the treatment of HIV infections.

An ideal route for the synthesis of the compound should produce the compound of formula (I) in high yields at a reasonable speed and at low cost with minimum waste materials and in a manner that is of minimum impact to the environment in terms of disposing of waste-materials and energy consumption.

We have found a new process for the synthesis of the compound of formula (I) with many advantages over previously known routes of synthesis. Such advantages include lower cost, less waste and more efficient use of materials. The new process enables advantageous preparation of the compound of formula (I) on a manufacturing scale.

The route of synthesis of the compound of formula (I) described in the specification of WO94/05639 is specifically described therein in examples 39A, 51A, 51B, 51C, 51D, 167 and 168. The overall yield from these examples is 33.2% of theory.

Generally the route described in WO94/05639 involves protecting the amino alcohol of formula (A) (Ex.39)

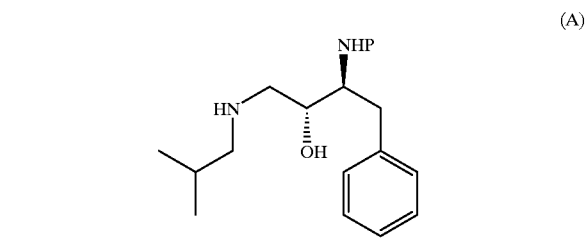

(A)

wherein P is a protecting group to form a compound of formula (B);

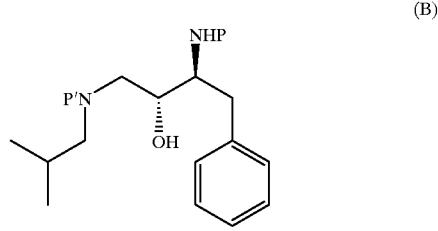

(B)

wherein P and P' are each independently a protecting group; deprotecting the compound of formula (B) to form a compound of formula (C) (Ex 51A);

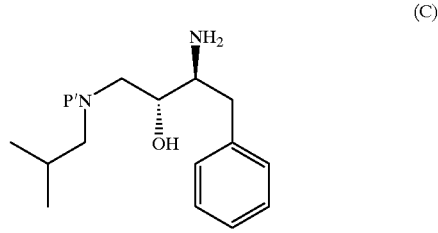

(C)

wherein P' is a protecting group;
forming a hydrochloride salt of compound (C) (Ex 51B) then reacting with N-imidazolyl-(S)-tetrahydrofuryl carbamate to form the compound of formula (D) (Ex 51C);

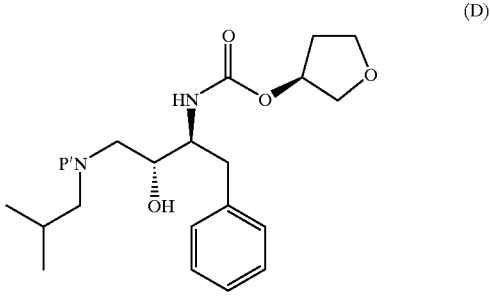

(D)

wherein P' is a protecting group;
deprotecting the compound of formula (D) (Ex 51D) wherein P' is a protecting group to form the compound of formula (D) wherein P' is H (Ex 51E); and coupling the resultant secondary amine on the compound of formula (D) to a p-nitrophenylsulphonyl group to form compound of formula (E) (Ex 167);

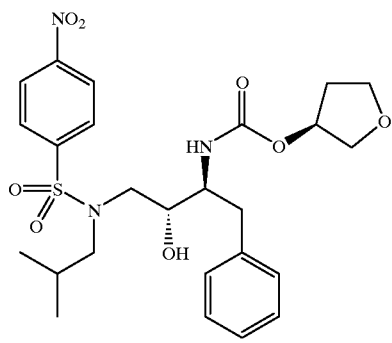

(E)

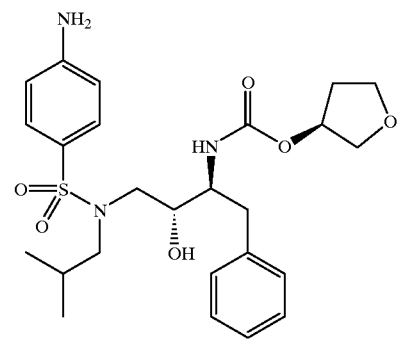

(I)

the resultant compound of formula (E) is then reduced to form the compound of formula (I) (Ex 168).

In summary, the process disclosed in WO94/05639 for producing the compound of formula (I) from the compound of formula (A) comprises 6 distinct stages:

1) protecting,
2) deprotecting,
3) reacting the resultant compound with an activated tetrahydrofuranol group,
4) deprotecting,
5) coupling with a p-nitrophenylsulfonyl group, and
6) reducing the resultant compound to form a compound of formula (I).

Applicants have now found a process by which the compound of formula (I) may be prepared on a manufacturing scale from the same starting intermediate, the compound of formula (A), in only 4 distinct stages instead of 6. In addition to the associated benefits of fewer stages, such as savings in time and cost, the improved process reduces the number of waste products formed. Furthermore, product may be obtained in a higher yield, of approximately 50% of theory.

The process of the present invention involves the following steps from the compound of formula (A) to the compound of formula (I);

1) coupling (A) with a p-nitrophenylsulfonyl group,
2) deprotecting the resultant compound,
3) reacting the resultant compound with a derivative of tetrahydrofuranol, and
4) reducing the resultant compound to form a compound of formula (I).

Ideally the tetrahydrofuranol derivative is prepared and coupled with the compound resulting from step 2) in a single step.

Therefore, presented as a feature of the present invention is a process for the preparation of the compound of formula (I)

comprising:
i) reacting a p-nitrophenylsulfonyl group with a compound of formula (A)

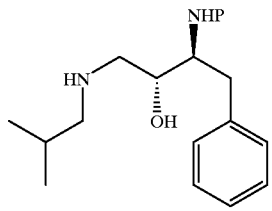

(A)

in which P is an amine-protecting group;
ii) deprotecting the resultant compound of step (i);
iii) reacting the resultant compound of step (ii) with a tetrahydrofuryloxy carbonyl group; or reacting the resultant compound of step ii) with phosgene, or equivalent, and reacting the resultant intermediate with (S)-tetrahydro-3-furanol; and
iv) reducing the resultant compound of step (iii) to form a compound of formula (I).

Preferably the protecting group P in the compound of formula (A) is an amine protecting group selected from alkyl, aryl, benzyl or heteryl carbamates, alkyl or aryl amides, or silyl groups. Most preferably P is a t-butyl carbamate.

Preferably step i) is carried out by treating the compound of formula (A) with a p-nitrophenylsulfonyl halide, preferably p-nitrobenzenesulfonyl chloride, in a suitable solvent selected from a ketone such as acetone, an ester such as ethyl acetate, an ether such as diethyl ether, an amine such as triethylamine, an amide such as dimethylformamide or dimethylacetamide, a chlorinated solvent such as dichloromethane and other solvents such as acetonitrile or toluene or mixtures thereof. Preferably, the reaction is carried out at a temperature in the range about 30° C. to reflux temperature, preferably in the range 70–90° C., with dimethylacetamide or toluene as the solvent.

Preferably step ii) is carried out in a suitable solvent selected from an alcohol such as ethanol, an ester such as ethyl acetate, an ether such as diethyl ether, a chlorinated solvent such as dichloromethane and other solvents such as acetonitrile or toluene or mixtures thereof. Ideally the reaction is carried out by treating a solution, for example an ethanol or toluene solution, of the resultant compound of step i) with an acid or base, for example a mineral acid such as hydrochloric acid or gaseous hydrogen chloride. Ideally the reaction is carried out at a temperature in the range about 500° C. to reflux temperature with hydrochloric acid. Preferably the reaction is carried out at atmospheric pressure.

Preferably the step ii) product is crystallised as a solvate, preferably an ethanolate, which is subsequently removed by drying. This provides advantages in yield.

The product of stage ii), (2R,3S)-N-(3-amino-2-hydroxy-4-phenylbutyl)-N-isobutyl-4-nitrobenzene sulphonamide hydrochloride and solvates thereof, are novel compounds and are presented as a further feature of the present invention.

Preferably step iii) is carried out by reacting the resultant compound of step ii) with a tetrahydrofuryloxy carbonyl group (prepared, for example, by reacting (S)-tetrahydro-3-furanol with 1,1'-carbonyidiimidazole, a chloroformate or phosgene), or reacting the resultant compound of step ii) with phosgene, or equivalent, to produce an isocyanate intermediate which can then react with (S)-tetrahydro-3-furanol or a precursor thereof. A suitable solvent may be selected from an ester such as ethyl acetate, an amide such as dimethylformamide, a chlorinated solvent such as dichloromethane and other solvents such as acetonitrile or toluene or mixtures thereof. Ideally the reaction is carried out in a single step by reacting (S)-tetrahydro-3-furanol with 1,1'-carbonyidiimidazole and the resultant compound of step ii) in ethyl acetate at a temperature in the range about 50° C. to reflux temperature. Preferably the reaction is carried out at atmospheric pressure.

Preferably step iv) is carried out by treating the resultant compound of step iii) with a reducing agent, for example a noble metal catalyst such as palladium, under a hydrogen atmosphere, in a suitable solvent, selected from an alcohol such as ethanol or isopropanol, a ketone such as acetone, an ester such as ethyl acetate, an amide such as dimethylformamide, and other solvents, such as tetrahydrofuran or mixtures thereof. Ideally the reaction is carried out in an alcohol, such as isopropanol, with a catalytic quantity of 5 or 10% palladium on carbon support at 0° C. to 60° C. under a hydrogen atmosphere.

The following scheme represents the process according to the invention and is not intended to limit the scope of the invention but is provided for illustration only.

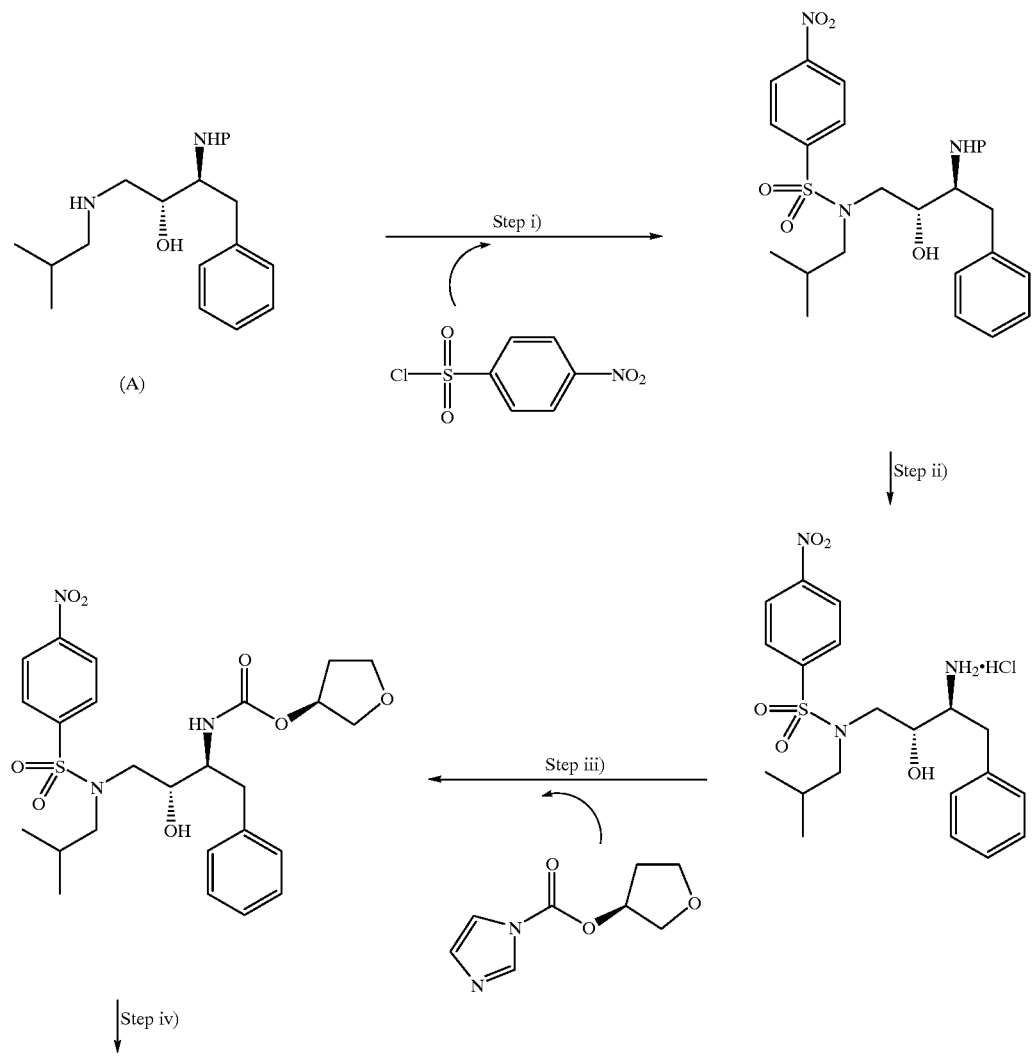

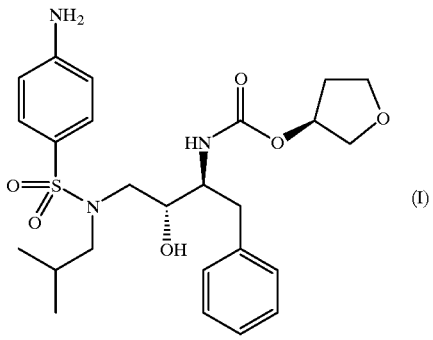

(I)

Compounds of formula (A) may be produced by the ring opening of a compound of formula (F)

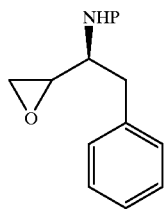

(F)

by addition of isobutylamine.

Compounds of formula (F) are known in the art, and may be produced by the methods described in Tetrahedron Letters (1995), 36 (19), 3317–20 and Tetrahedron Letters (1995), 36 (31), 5453–6.

In order that the invention may be more fully understood the following examples are presented by way of illustration only.

In the Intermediates and Examples unless otherwise stated:

All temperatures refer to ° C. Proton Magnetic Resonance ($^1$H-NMR) spectra were recorded at 400, 500 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). The following abbreviations are used in text: THF=tetrahydrofuran, EtOH=ethanol, DMA=dimethylacetamide, TEA HCl=triethylamine hydrochloride.

EXAMPLES

Example 1

(1S,2R)-tert-butyl N-[1-benzyl-2-hydroxy-3-(isobutylamino)propyl]carbamate (127.77 g, 379.7 mmol) was heated in toluene (888 ml) to 80° C. and triethylamine (42.6 g, 417.8 mmol) added. The mixture was heated to 90° C. and a solution of p-nitrobenzene sulphonyl chloride (94.3 g, 425.4 mmol) in toluene (250 ml) was added over 30 minutes then stirred for a further 2 hours. The resultant solution of the nosylated intermediate {(1S,2R)-tert-butyl N-[1-benzyl-2-hydroxy-3-(N-isobutyl-4-nitrobenzenesulphonamido)propyl]carbamate } was then cooled to 80° C. The solution was maintained at approximately 80° C., and concentrated hydrochloric acid (31.4 ml, 376.8 mmol) was added over 20 minutes. The mixture was heated to reflux (approx 86° C.) and maintained at this temperature for an hour then a further quantity of concentrated hydrochloric acid (26.4 ml, 316.8 mmol) was added. Solvent (water and toluene mixture) was removed from the reaction mixture by azeotropic distillation (total volume of solvent removed approx 600 ml), and the resultant suspension was cooled to 70–75° C. Denatured ethanol (600 ml) was added, and the solution was cooled to 20° C. The mixture was further cooled to approximately −10° C. and the precipitate formed was isolated by filtration, washed with denatured ethanol (50 ml) and dried at approximately 50° C., under vacuum, for approximately 12 hours, to give (2R,3S)-N-(3-amino-2-hydroxy-4-phenylbutyl)-N-isobutyl-4-nitrobenzene sulphonamide hydrochloride (160 g; 73% of theory yield corrected for assay). NMR: $^1$H NMR (300Mhz, dmso-d$_6$): 8.37(2H, d, J=9 Hz), 8.16(NH$_3^+$s), 8.06(2H, d, J=9 Hz), 7.31(5H, m), 5.65(1H, d, J=5 Hz), 3.95(1H, m), 3.39(2H, m), 2.95(5H, m), 1.90(1H, m), 0.77(6H, dd, J=21 Hz and 6 Hz).

1,1'-carbonyidiimidazole (27.66 kg, 170.58 mol) was added to ethyl acetate (314.3 kg) with stirring to give 3-(S)-tetrahydrofuryl imidazole-1-carboxylate. (S)-3-hydroxytetrahydrofuran (157 kg, 178.19 mol) was added over 30 minutes, washed in with ethyl acetate (9.95 kg), then the mixture was stirred for a further hour. (2R,3S)-N-(3-amino-2-hydroxy-4-phenylbutyl)-N-isobutyl-4-nitrobenzene sulphonamide hydrochloride (65.08 kg, 142.10 mol) was added and the mixture heated to reflux for approximately 22 hours. The solution was cooled slightly, and denatured ethanol (98 l) was added. The solution was stirred at 60° C. for 10 minutes then cooled and the product allowed to crystallise. The mixture was cooled to <10° C. and stirred for 2 hours. The product was isolated by filtration, washed with denatured ethanol (33 l) and dried at approximately 50° C., under vacuum to give (3S)-tetrahydro-3-furyl N-[(1S,2R)-1-benzyl-2-hydroxy-3-(N-isobutyl-4-nitrobenzene sulphonamido)propyl]carbamate in a yield of 82% of theory.

NMR: $^1$H NMR (500 Mhz, dmso-d$_6$): 8.38(2H, d, J=9Hz), 8.06(2H, d, J=9 Hz), 7.20(6H, m), 5.02(1H, d, J=5 Hz), 4.94(1H, m), 4.35(EtOH, broad s), 3.71(EtOH, q), 3.65(1H, m), 3.60(1H, m), 3.51(2H, broad m), 3.40(2H, m), 3.15(1H, dd, J=8 Hz and 14 Hz), 3.07(1H, dd, J=8 Hz and 15 Hz), 2.94(2H, m), 2.48(1H, m), 2.06(1H, m), 1.97(1H, m), 1.78 (1H, m), 1.05(EtOH, t), 0.83(6H, dd, J=7 Hz and 16 Hz).

Product from the above stage (80.0 g, 149.4 mmol) was hydrogenated in isopropanol (880 ml) with 5% palladium on carbon (16 g, of a wet paste) and hydrogen pressure (approx 0.5 to 1.5 bar) at 25–50° C. for approximately 5 hours. The mixture was cooled and the catalyst removed by filtration. The solution was distilled to a volume of approximately 320 ml and water (80 ml) was added. This solution was divided into two for the crystallisation step.

To half of the above solution, decolourising charcoal (2 g) was added, the mixture stirred at approximately 32° C. for 4 hours, then filtered. The filtercake was washed with isopropanol (20 ml) then further water (40 ml) was added to the filtrate. The solution was seeded to induce crystallisation and stirred for 5 hours. Water (130 ml) was added slowly over 1 hour then the mixture was stirred for 4 hours. The resultant slurry was cooled to approximately 20° C. and the product was isolated by filtration and washed with a 1:4 mixture of isopropano/water (120 ml). The product was dried at approximately 50° C., under vacuum, for approximately 12 hours to give (3S)-tetrahydro-3-furyl N-[(1S,2R)-3-(4-amino-N-isobutylbenzenesulphonamido)-1-benzyl-2-hydroxypropyl] carbamate (30.3 g; 80% of theory yield).

NMR: $^1$H NMR (300 Mhz, dmso-$d_6$): 7.39(2H, d, J=9 Hz), 7.18(6H, m), 6.60(2H, d, J=9 Hz), 6.00(2H, s), 4.99 (1H, d, J=6 Hz), 4.93(1H, ddt), 3.64(5H, m), 3.34(1H, m), 3.28(1H, dd, J=14 Hz and 3 Hz), 3.01(1H, m, J=14 Hz and 3 Hz), 2.91(1H, m), 2.66(2H, m), 2.50(1H, m), 2.05(1H, m), 1.94(1H, m), 1.78(1H, m), 0.81(6H, dd, J=16 Hz and 7 Hz). m/z: 506.2(M+H$^+$)

Example 2

Alternative Preparation of (2R, 3S)-N-(3-amino-2-hydroxy-4-phenylbutyl)-N-isobutyl-4-nitrobenzene sulphonamide hydrochloride (1S,2R)-tert-butyl N-[1-benzyl-2-hydroxy-3-(isobutylamino)propyl] carbamate (212.1 kg, 630.36 mol) was stirred in dimethylacetamide (259.1 kg) at 40° C. and triethylamine (70.9 kg, 700.66 mol) was added. A solution of p-nitrobenzene sulphonyl chloride (153.6 kg, 693.08 mol) in tetrahydrofuran (205.3 kg) was added over 2 hours 35 mins, then stirred for a further hour, maintaining the reaction temperature at 40° C. The mixture was cooled to 30° C. and water (1079 l) was added to the resultant solution. The solution was then cooled to 25° C. The mixture was stirred for 1 hour then the product was isolated by filtration, washed with water (332 l) and then denatured ethanol (664 l) to give damp (1S,2R)-tert-butyl N-[1-benzyl-2-hydroxy-3-(N-isobutyl-4-nitrobenzene-sulphonamido)propyl] carbamate (618 kg).

NMR: $^1$H NMR (500 Mhz, dmso-$d_6$): 8.36(2H, d, J=9 Hz), 8.05(2H, d, J=9 Hz), 7.18(5H, m), 6.67(1H, d, J=9 Hz), 5:02(1H, broad s), 3.63(3H, broad m), 3.63(EtOH, broad s), 3.58(THF, broad m), 3.44(EtOH, q), 3.10(2H, m), 2.93(2H, m), 2.93(DMA, s), 2.78(DMA, s), 2.48(1H, m), 1.97(1H, m), 1.95(DMA, s), 1.74(THF, m), 1.23(9H, s), 1.18(TEA HCl, t), 1.05(EtOH, t), 0.82(6H, dd, J=6 Hz and 12 Hz)

The damp product of the above stage (602.5 kg, 423.9 mol corrected for solvent content) was stirred in denatured ethanol (1646 l) and concentrated hydrochloric acid (104.6 kg) was added. The mixture was heated to reflux and maintained at this temperature for 3 hours. The solution was then cooled to approximately 35° C. and seeded, then cooled further to –5° C. to complete the crystallisation. The product was isolated by filtration, washed with denatured ethanol (221.7 l) and dried at approximately 50° C., under vacuum, for approximately 6 hours to give (2R,3S)-N-(3-amino-2-hydroxy-4-phenylbutyl)-N-isobutyl-4-nitrobenzene sulphonamide hydrochloride (153.8 kg; 80% of theory yield).

NMR: $^1$H NMR (500 Mhz, dmso-$d_6$): 8.37(2H, d, J=9 Hz), 8.18(NH$_3^+$, s), 8.06(2H, d, J=9Hz), 7.31(5H, m), 5.63 (1H, d, J=5 Hz), 3.93(1H, m), 3.45(1H, m), 3.39(1H, dd, J=4 Hz and 15 Hz), 3.06(2H, m), 2.98(1H, m), 2.87(2H, m), 1.90(1H, m), 0.77(6H, dd, J=21 Hz and 6 Hz)

The product of the above stage may be used to form the compound of formula (I) in a similar manner to that described in example 1 above.

Example 3

Alternative Preparation of (2R,3S)-N-(3-amino-2-hydroxy-4-phenylbutyl)-N-isobutyl-4-nitrobenzene sulphonamide hydrochloride (1S,2R)-Tert-butyl N-[1-benzyl-2-hydroxy-3-(N-isobutyl4-nitrobenzene sulphonamido)propyl]carbamate (18 kg, 34.5 mol; prepared in a similar manner to that described in Example 2) was dried, then stirred in ethyl acetate (62.6 kg) at 15° C. Hydrogen chloride gas (approx 9 kg) was bubbled into the mixture and the reaction stirred below 40° C. for approximately 4 hours. The reaction was cooled to approximately 5° C. The product was isolated by filtration, washed with cold ethyl acetate (20 l) then with methyl tert-butyl ether (37.8 l), and dried at approximately 50° C. under vacuum for approximately 12 hours to give (2R,3S)-N-(3-amino-2-hydroxy -4-phenylbutyl)-N-isobutyl-4-nitrobenzene sulphonamide hydrochloride (13.6 kg; 86% of theory yield).

The product of the above stage may be used to form the compound of formula (l) in a similar manner to that described in example 1 above.

What is claimed is:

1. A process for the preparation of the compound of formula (I)

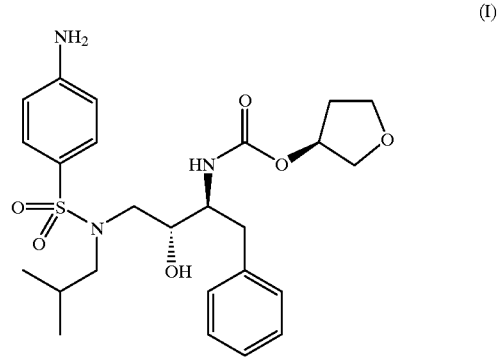

(I)

comprising:
  i) reacting a p-nitrophenylsulfonyl group with a compound of formula (A)

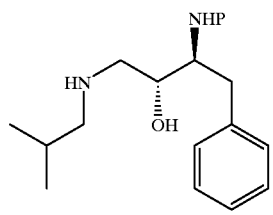

(A)

in which P is an amine-protecting group;
  ii) deprotecting the resultant compound of step i);
  iii) reacting the resultant compound of step (ii) with a tetrahydrofuryloxy carbonyl group; or reacting the resultant compound of step ii) with phosgene, or equivalent, and reacting the resultant intermediate with (S)-tetrahydro-3-furanol; and
  iv) reducing the resultant compound of step iii) to form a compound of formula (I).

2. A process as claimed in claim 1 in which the protecting group P in the compound of formula (A) is an alkyl, aryl, benzyl or hetero carbamate, alkyl or aryl amide, or silyl group.

3. A process as claimed in claim 2 in which the protecting group P in the compound of formula (A) is t-butyl carbamate.

4. A process as claimed in claim 1 in which the p-nitrophenylsulfonyl group in step i) is a p-nitrophenyisulfonyl halide.

5. A process as claimed in claim 1 in which step i) is carried out in dimethylacetamide or toluene.

6. A process as claimed in any preceding claim in which step ii) is carried out in ethanol or toluene.

7. A process as claimed in claim 1 in which the step ii) product is crystallised as a solvate.

8. A process as claimed in claim 1 in which step iii) is carried out by reacting (S)-tetrahydro-3-furanol with 1,1'-carbonyidiimidazole and the step ii) product in a single step.

9. A process as claimed in claim 8 in which step iii) is carried in ethyl acetate.

10. A process as claimed in claim 1 in which step iv) is carried out by treating the step iii) product with palladium under a hydrogen atmosphere.

11. A process as claimed in claim 10 in which step iv) is carried out in isopropanol.

12. The compound (2R,3S)-N-(3-amino-2-hydroxy-4-phenylbutyl)-N-isobutyl-4-nitrobenzene sulphonamide hydrochloride and solvates thereof.

* * * * *